United States Patent [19]

Niezink et al.

[11] Patent Number: 5,785,680
[45] Date of Patent: Jul. 28, 1998

[54] INJECTOR AND OBJECT TO BE INJECTED BY THE INJECTOR

[75] Inventors: Herman Niezink, Wierden; Franciscus H. C. Benning, Almelo; Leo K. Kruit, Maarssenbroek, all of Netherlands

[73] Assignee: Texas Instruments Incorporated, Dallas, Tex.

[21] Appl. No.: 689,532

[22] Filed: Aug. 8, 1996

Related U.S. Application Data

[63] Continuation of Ser. No. 259,232, Jun. 13, 1994, abandoned.

[51] Int. Cl.$^6$ .................................................. A61M 31/00
[52] U.S. Cl. .......................... 604/57; 604/187; 606/116; 606/117
[58] Field of Search .................... 604/57, 59, 60, 604/68, 72, 181, 130, 188, 192, 187, 151, 183; 623/16; 128/903; 424/423; 340/573; 606/116–117, 75, 232; 124/22, 73; 273/418

[56] References Cited

U.S. PATENT DOCUMENTS

| | | | |
|---|---|---|---|
| 1,868,308 | 7/1932 | Brumfield | 604/59 |
| 2,348,337 | 5/1944 | Francis | 604/130 |
| 3,565,435 | 2/1971 | Bear. | |
| 4,326,524 | 4/1982 | Drake, Jr. et al. | 604/130 |
| 4,672,967 | 6/1987 | Smith | 128/330 |
| 4,675,683 | 6/1987 | Robinson et al. | |
| 4,697,575 | 10/1987 | Horowitz | 128/1.2 |
| 4,920,413 | 4/1990 | Nakamura et al. | |
| 5,053,774 | 10/1991 | Schuermann et al. | 342/44 |
| 5,527,342 | 6/1996 | Pietrzak et al. | |
| 5,545,180 | 8/1996 | Le et al. | |
| 5,580,569 | 12/1996 | Giampapa. | |
| 5,584,819 | 12/1996 | Kopfer. | |

FOREIGN PATENT DOCUMENTS

| | | | |
|---|---|---|---|
| 0255123 | 2/1988 | European Pat. Off. | |
| 0497575 | 8/1992 | European Pat. Off. | 36/12 |

*Primary Examiner*—Mark Bockelman
*Attorney, Agent, or Firm*—Rebecca Mapstone-Lake; James C. Kesterson; Richard L. Donaldson

[57] ABSTRACT

Apparatus for introducing a transponder in a living being wherein the transponder itself is outfitted with a sharpened member attached to the injection end of a transponder. The sharpened member comes in contact with the skin before the transponder thereby creating an opening in the skin such that the transponder can be blunt edged and move into the opening easily. The sharpened member is preferably constructed of a bio-compatible, preferably biodegradable material which may carry medication additionally.

20 Claims, 1 Drawing Sheet

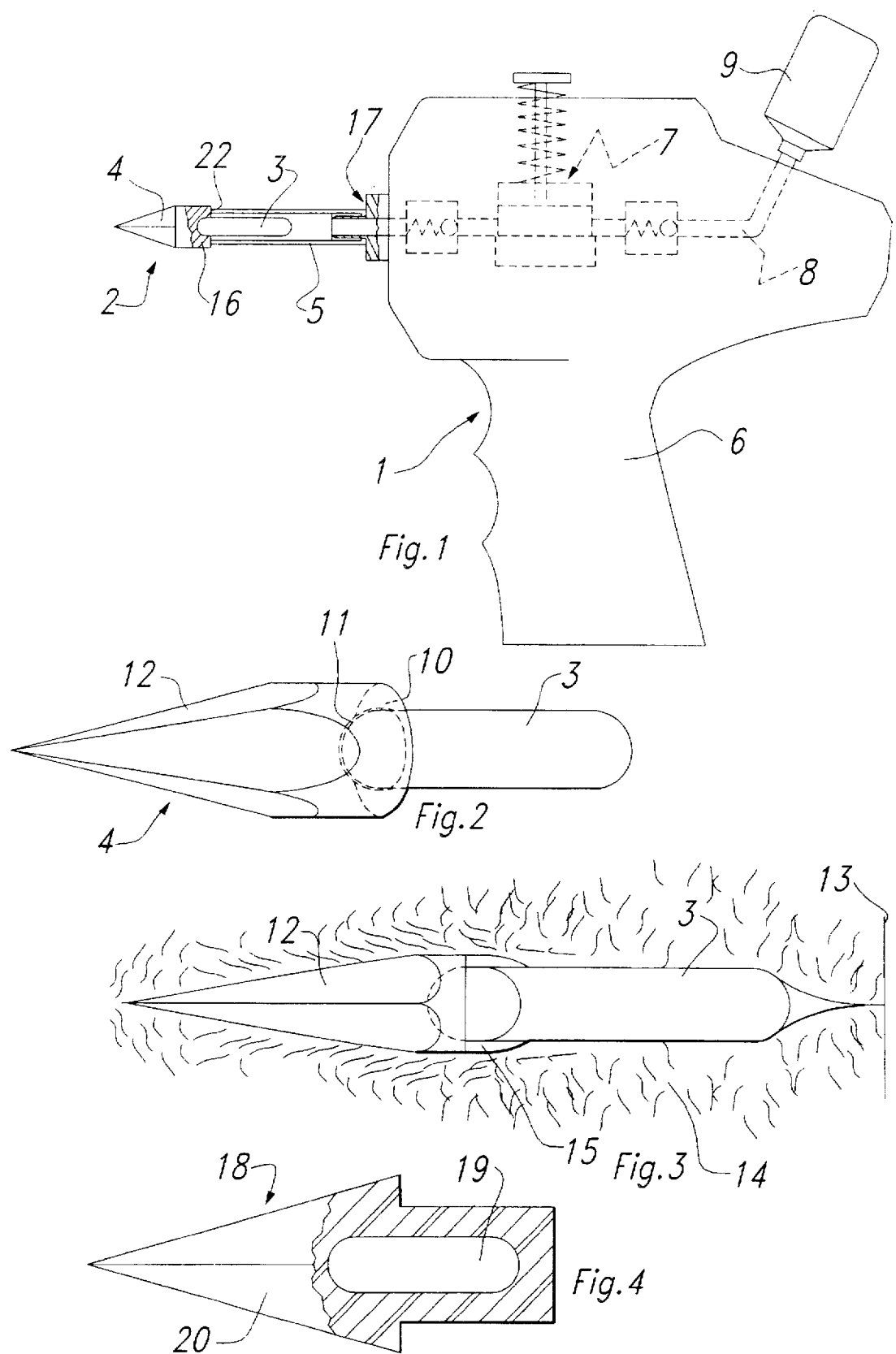

INJECTOR AND OBJECT TO BE INJECTED BY THE INJECTOR

This application is a Continuation of application Ser. No. 08/259,232, filed Jun. 13, 1994 now abandoned.

BACKGROUND OF THE INVENTION

The invention relates to an injector for introducing an object, such as a transponder, in a living being, comprising a housing to which an injector tube is connected for receiving and guiding the object.

Such an injector is generally known in the prior art. Objects, such as transponders are injected in animals, e.g. for identification purposes. The opening in the skin of the animal is realized or achieved in that the tip of the injector tube in such prior art injectors is sharpened. This generally means that the injector is a hollow needle of which the end face is sharpened to penetrate the animal's skin and thereby provide an opening. Because of the sharpened end during non-use, there is a substantial danger that the operators using the injector can hurt themselves or others because of the tip of the needle. In some prior art injectors to prevent these problems, the needle is made retractable. However, due to the dirt and the nature of the skin of several animals, high requirements are set on the material from which the needle tip is manufactured. Further, wear often takes place after a relative low number of transponders have been injected such that the force to penetrate the skin will increase and the accuracy of placing of the transponder will decrease. Furthermore, there is the problem of cross contamination between animals through the needle tip.

The invention aims to provide an improved injection technique which can be used together with a new transponder to avoid the drawbacks relating to the presence of a sharp needle tip.

SUMMARY OF THE INVENTION

Other objects and advantages will be obvious and will in part appear hereinafter, and will be accomplished by the present invention which comprises an injector having a support housing and an injector tube. The injector tube is supported by said housing at one end and has an inside diameter for receiving and guiding an elongated object such as a transponder to be injected. The unsupported end of the injector tube has a blunt circumferential edge. The transponder or elongated object to be injected has a circumference which fits into and is supported by the injector tube. According to one embodiment, a sharpened tip member is secured to the elongated object and is suitable for penetrating the skin and tissue of the living being.

The invention operates on the principal that the object to be injected is provided with a sharp tip so that it is not longer necessary that an opening or incision be cut into the living being with the injector tube. Thus, the primary purpose of the injector tube is to act as a guide for the object or transponder which is to be introduced. This means that the free extremity of the injector tube can be blunt so that during non-use it is completely safe and no separate costly measures have to be taken to prevent this sharpened end from contacting the operators or other persons. On the other hand, such a device is extremely simple. The sharpened tip member enters the living being together with the transponder or other object to be injected and is only used a single time. This means that the danger of cross contamination is reduced whilst abrasive conditions during introduction of the tip do not have any effect on the service life of the sharpened tip because of its single use.

According to one embodiment of the invention, the injector tube is removable from the casing or support housing of the injector. This means that a new injector tube can easily be placed on the casing thereby further reducing the danger of cross contamination.

To increase the acceptance of the transponder by the living being and to avoid infection, an injector liquid dosing means are provided which is connected to the injector tube. During or before each introduction of the transponder in the living being a liquid such as a disinfectant can be metered to prevent infection during the introduction of the transponder. Of course, the liquid could be any other selected medication.

BRIEF DESCRIPTION OF THE DRAWINGS

The invention will be more clearly understood with reference to the following description as illustrated in the enclosed drawings, wherein;

FIG. 1 shows an injector apparatus according to the invention together with a transponder;

FIG. 2 shows a detailed view of the transponder and the sharpened tip member according to the invention;

FIG. 3 shows the transponder and tip according to the invention introduced subcutaneous in an animal; and FIG. 4 shows an alternate embodiment of the transponder according to the invention.

BEST KNOWN MODE FOR CARRYING OUT THE INVENTION

In FIG. I an injector according to the invention is generally indicated at 1 having an injectable object 2. Injectable object 2 comprises a transponder member 3 as is generally known in the art (such as, for example as described in U.S. Pat. No. 5,053,774) and a sharpened transponder tip 4. This transponder member 3 can be any transponder having either a glass or plastic housing and is usually of elongated shape having rounded extremities. Tip 4 is provided with four cutting ribs 12 as is clear from FIG. 2. Connection between tip 4 and transponder member 3 is preferably realized by a layer 11 of glue. In a preferred embodiment, tip 4 is made from bone material and layer 11 has good adhesion properties with regard to such bone material and the material from which the transponder housing (i.e., glass or plastic) is constructed.

As shown in FIG. 1, injector 1 includes an injector tube 5 connected to and supported by a casing or support housing 6. Injector tube 5 includes a blunt circumferential edge 22 at its unsupported or free extremity. The free extremity of injector tube 5 functions to support and guide the transponder. In a preferred embodiment, a transition area or abutment face 10 is provided between the rear end of the tip 4 and the front end of the transponder member. The blunt end surface 22 of the extremity of the injector tube 5 rests on this abutment face 10 and forces exerted on the grip or housing 6 of the injector 1 are transmitted through this extremity 22 to the sharpened tip member 2 located at the front of transponder 3 whilst the vulnerable transponder 3 being received in the injector tube is not subjected to these forces and is protected against damage during injection.

More specifically, as is clear from FIG. 2, the outer circumference of the non-sharpened end of tip 12 is somewhat larger than the outer circumference of transponder member 3 adjacent thereto. This difference in circumference of the tip and transponder creates abutment face 10. This abutment face 10 is dimensioned such that the blunt extremity 22 of injector tube 5 (see FIG. 1) bears against this abutment face. Forces during introduction are directly transferred from the injector tube 5 to the sharpened tip member 2 and not through the transponder member 3. This is superior to prior art devices wherein a push rod is used inside injector tube 5.

Also in a preferred embodiment, injector tube 5 is connected to housing 6 through a quick connecting means 17. This means that injector tube 5 can be easily replaced by a new unused tube. Further, because the free extremity 22 of the injector tube 5 is unsharpened, the costs for producing such a tube are relatively low. In a further embodiment, the interior of the hollow tube 5 is connected to pump 7 which is in turn connected to reservoir 9 through conduit 8. This reservoir 9 contains medicine, such as a disinfectant agent, which can be introduced by pumping into injector tube 5 and around transponder member 3. During introduction, the single use tip 4 cuts an opening in skin 13 of the animal (FIG. 3). To facilitate introduction of the transponder, the tip is provided with at least two external ribs. These external ribs make an incision such that skin flaps result and punching out or loosening of parts of the skin is prevented during introduction of the transponder decreasing the danger of infection of the animal during healing of the wound. In a preferred embodiment, four (4) sharp ribs 12 are provided. Because of the presence of four ribs 12, two cross cuts are realized in skin 13 resulting in four flaps which are bent inwardly into the animal and after introduction of the transponder move outwardly again such that no parts of the skin will be introduced in the animal. In FIG. 3, the position of the transponder in tissue 14 is shown. Because of the presence of abutment surface 10 on position 15 in tissue 14, a restriction will grow after introduction of the transponder preventing the transponder from moving back in the direction to the skin.

To further prevent infections and rejection of the transponder, the tip is preferably fabricated from a material which is bio-compatible with the living being. An example for such bio-compatible material is bone material. After machining to the desired shape and disinfection, e.g. by boiling, it has been shown that this material is very suitable for use as tip material. Through sterilizing by boiling only the harder part of the bone material will remain and the marrow parts will disappear. This harder part will disintegrate after introduction into the animal. In addition to preparing a tip by machining from bone material, it is also possible to first grind such bone material and to pressshape the related tip. Because bone material is a natural material, it is easily accepted by animals. It has been observed that after several weeks of introduction at least the sharpest parts of the tips will be dissolved or eroded. This prevents the transponder from wandering through the animal. The abutment surface 10 described above between the tip and the transponder member also acts as barb surface preventing rearward movement of the transponder after introduction. Of course, a medication can be added to or impregnated into the tip such as a disinfectant. In view of further miniaturization of the transponder member, it is quite possible for the tip to also act as a support body for this transponder member. This means that in the tip an opening or cavity is provided in which the transponder member is received. It has been observed that after introduction, the end of the tip irritates the tissue of the animal such that its rejection mechanism will become active around the wound and provide encapsulation. However, before the rejection mechanism is able to reject the transponder, the free extremity of the tip is degraded considerable and will be kept in its position. The connection between tip and transponder member is such that if a non-axial load is inserted it will break through the layer 11 of glue.

As described above, the bone material tip can be produced by first grinding of bones and afterwards boiling during at least 24 hours. During boiling the marrow material will substantially disintegrate and the harder part of the bone remains. After that disinfectant, such as iodine, is added and the bone material is pressed to the tip shape. It is glued with bone cement to the transponder member.

It has been observed that after introduction into a living being after about two weeks, the most sharpened parts are disappeared and the remaining tip has the properties of cartilage.

In FIG. 4, a further embodiment is shown wherein the transponder member 19 is of a size such that it can easily be received in body 20 of the transponder 18. Tip and body are made from the same material.

Although the invention is described above relating to a preferred embodiment, it will be clear for the person skilled in the art that many amendments can be made without leaving the scope of protection as defined in the appended claims.

It is, for example, possible to realize the tip from any bio-compatible material not being bone material.

What is claimed is:

1. Apparatus for injecting objects into a living being comprising:

an injector comprising a support housing and an injector tube having a selected inside diameter for receiving and guiding said objects being injected, said injector tube having a first end connected to and supported by said support housing and a further end extending away from said housing, said further end defining a blunt circumferential edge;

an elongated object to be injected and having a front end and a back end and a circumference able to be at least partially inserted into and supported by said injector tube, and a tip member having a sharpened end and a rear portion wherein said rear portion has an outer circumference and an inner circumference cut from said rear portion and is secured to one end of said elongated object, said sharpened end suitable for penetrating the skin of said living being, and wherein a transition area is provided between the rear portion of the tip member and the front end of the object to be injected, wherein the outer circumference of the tip member at its rear portion extends beyond the circumference of the front end of the object to be inserted and further, the front end of said object fits conformably within said inner circumference cut from said rear portion of said tip member.

2. Apparatus according to claim 1, wherein the injector tube is removable from the housing.

3. The apparatus according to claim 1, wherein said sharpened tip member is provided with at least two external ribs.

4. The apparatus according to claim 1, wherein said sharpened tip member comprises a material which is bio-compatible with the living being.

5. The apparatus according to claim 4, wherein the bio-compatible material comprises bone material.

6. The apparatus according to claim 4, wherein the biocompatible material comprises biodegradable material.

7. The apparatus according to claim 1, wherein said tip member contains a medication.

8. The apparatus according to claim 7, wherein the medication comprises a disinfectant.

9. The apparatus according to claim 1, wherein the transition area defines an abutment surface of said tip member through which a force can be applied from said support housing to said blunt circumferential edge of said injector tube to said abutment surface of said tip member so as to penetrate the skin of said living being.

10. The apparatus according to claim 1, wherein said elongated member is a transponder.

11. Apparatus for injecting objects into a living being comprising:

an injector comprising a support housing and an injector tube having a selected inside diameter for receiving and guiding said objects being injected, said injector tube having a first end connected to and supported by said support housing and a further end extending away from said housing, said further end defining a blunt circumferential edge;

an elongated object to be injected and having a front end and a back end and a circumference able to be at least partially inserted into and supported by said injector tube, and a tip member having a sharpened end a rear portion wherein said rear portion has an outer circumference and an inner circumference cut from said rear portion and is secured to one end of said elongated object wherein said elongated object fits conformably within said inner circumference, said sharpened end suitable for penetrating the skin of said living being, and further comprising a liquid dosing means connected to said injector tube for providing a medicinal liquid to the penetrating site of the living animal.

12. The apparatus of claim 11, wherein said elongated object is a transponder.

13. The apparatus of claim 4 wherein said liquid dosing means comprises a reservoir for containing a disinfectant, a pump, and a conduit connecting said injector tube, said pump and said reservoir.

14. Apparatus according to claim 11, wherein the injector tube is removable from the housing.

15. The apparatus according to claim 11, wherein said sharpened tip member is provided with at least two external ribs.

16. The apparatus according to claim 11, wherein said sharpened tip member comprises a material which is bio-compatible with the living being.

17. The apparatus according to claim 16, wherein the bio-compatible material comprises bone material.

18. The apparatus according to claim 16, wherein the bio-compatible material comprises biodegradable material.

19. The apparatus according to claim 11, wherein said tip member contains a medication.

20. The apparatus according to claim 19, wherein the medication comprises a disinfectant.

* * * * *